United States Patent
McCrory et al.

(10) Patent No.: US 8,656,521 B2
(45) Date of Patent: Feb. 25, 2014

(54) GOGGLE LENS COVER

(75) Inventors: Jenna A. McCrory, Driggs, ID (US); E. Brooks Detchon, Driggs, ID (US)

(73) Assignee: JB Creations LLC, Wakefield, RI (US)

( * ) Notice: Subject to any disclaimer, the term of this patent is extended or adjusted under 35 U.S.C. 154(b) by 166 days.

(21) Appl. No.: 13/118,980

(22) Filed: May 31, 2011

(65) Prior Publication Data

US 2012/0005811 A1 Jan. 12, 2012

Related U.S. Application Data (60) Provisional application No. 61/399,369, filed on Jul. 12, 2010.

(51) Int. Cl.
  *A61F 9/02* (2006.01)
  *A61F 9/00* (2006.01)
(52) U.S. Cl.
  USPC .......................................... 2/426; 2/452; 2/15
(58) Field of Classification Search
  USPC ............... 206/5; 2/426, 452, 13, 15; 150/154
  See application file for complete search history.

(56) References Cited

U.S. PATENT DOCUMENTS

| | | | | |
|---|---|---|---|---|
| 775,381 A | * | 11/1904 | Newbold | ............................ 2/454 |
| 2,106,561 A | | 1/1938 | Beiter | |
| 2,557,552 A | * | 6/1951 | Martin | ................................. 2/10 |
| 3,416,202 A | | 12/1968 | Sasaoka | |
| 3,677,270 A | | 7/1972 | Goodman | |
| 3,898,717 A | | 8/1975 | Schwartz | |
| 4,290,522 A | * | 9/1981 | Takasaki | ............................ 206/5 |
| 4,606,453 A | * | 8/1986 | Burns | ................. 206/5 |
| 4,793,030 A | | 12/1988 | Hirsch | |
| 4,919,258 A | * | 4/1990 | Perretta | .............................. 206/5 |
| 4,953,695 A | * | 9/1990 | Tallman | ............................ 206/5 |
| 5,014,846 A | * | 5/1991 | Walker et al. | ...................... 206/5 |
| 5,032,019 A | * | 7/1991 | Burchett | ........................ 351/158 |
| 5,052,550 A | * | 10/1991 | Pfenning | ............................ 206/5 |
| 5,102,216 A | * | 4/1992 | Mitchell | ........................ 351/156 |
| 5,151,778 A | * | 9/1992 | Conley | ........................... 351/156 |
| 5,213,241 A | | 5/1993 | Dewar et al. | |
| 5,299,682 A | * | 4/1994 | Tatar | ................................. 206/5 |
| 5,344,002 A | * | 9/1994 | Baczkowski | ...................... 206/5 |
| 5,553,321 A | * | 9/1996 | Cassel | ................................. 2/13 |
| 5,593,024 A | * | 1/1997 | Seiler | ................................. 206/5 |
| 5,687,837 A | * | 11/1997 | Seiler | ................................. 206/5 |
| 5,722,437 A | | 3/1998 | Chang | |

(Continued)

FOREIGN PATENT DOCUMENTS

WO WO 2006/003415 1/2006

OTHER PUBLICATIONS

International Search Report for PCT Application No. PCT/US2011/043512, mailed Dec. 6, 2011, 3 pages.

(Continued)

*Primary Examiner* — Amber Anderson
(74) *Attorney, Agent, or Firm* — Sheridan Ross P.C.

(57) ABSTRACT

A cover is provided that is comprised of a fabric panel and two members or mechanisms that selectively connect to the strap of a goggle device. The panel is made of a lens-safe, flexible, and resilient material which allows it to fit most size goggles. Further, top and bottom panels may have elastic inner edges, which help the cover to contour to the shape of the goggle. In addition, a lens cleaning cloth is interconnected to the top panel.

16 Claims, 5 Drawing Sheets

(56) References Cited

U.S. PATENT DOCUMENTS

| | | | |
|---|---|---|---|
| 5,735,393 A * | 4/1998 | Shiue et al. | 206/5 |
| 5,878,443 A | 3/1999 | Seiler | |
| 5,913,416 A * | 6/1999 | Rothan | 206/5 |
| 6,038,706 A * | 3/2000 | Seiler | 2/426 |
| 6,439,379 B2 * | 8/2002 | Taormina | 206/5 |
| 6,640,346 B2 * | 11/2003 | Dufresne | 2/424 |
| 6,826,784 B2 * | 12/2004 | Patire | 2/433 |
| 6,907,617 B2 | 6/2005 | Johnson | |
| D522,563 S * | 6/2006 | Lawrence et al. | D16/340 |
| 7,131,533 B2 * | 11/2006 | Anderson et al. | 206/5 |
| 7,770,721 B2 * | 8/2010 | Orner | 206/5 |
| 8,151,374 B2 * | 4/2012 | Wilcox | 2/426 |
| 8,272,071 B2 * | 9/2012 | Kaiser | 2/15 |
| 2003/0145368 A1 * | 8/2003 | Johnson | 2/434 |
| 2004/0182412 A1 | 9/2004 | Vogel | |
| 2009/0000964 A1 * | 1/2009 | Orner | 206/5 |
| 2009/0026095 A1 | 1/2009 | Lofland et al. | |
| 2009/0307828 A1 * | 12/2009 | Ludlow | 2/431 |

OTHER PUBLICATIONS

Written Opinion for PCT Application No. PCT/US2011/043512, mailed Dec. 6, 2011, 6 pages.

* cited by examiner

GOGGLE LENS COVER

This application claims the benefit of U.S. Provisional Patent Application Ser. No. 61/399,369, filed Jul. 12, 2010, the entire disclosure of which is incorporated by reference herein.

FIELD OF THE INVENTION

Embodiments of the present invention generally relate to a protective cover for snow sport, tactical, and motor sports goggles. One embodiment of the present invention further includes a lens cleaning cloth.

BACKGROUND OF THE INVENTION

Goggle lenses, especially the inner surface that is worn closest to the wearer's eyes are susceptible to damage when exposed to snow, dust, dirt, grease, or passive contact of any kind. Thus protective covers are often used that are made of a material that will not damage the lens.

Further, notwithstanding manufacturer's instructions directing users to clean lenses with only a cloth comprised of a non-scratching material, some wearers choose to clean these goggles with their goggle cover, which is often made of polar fleece, which attracts lint and dust. If a wearer uses this type of cover in an attempt to clean inner lens surface, they will most likely damage the lens. The best way to clean the inner and outer lens surface is with an ultra-fine, tightly woven material such as microfiber.

In addition, many existing goggle covers are difficult to interconnect to goggles. It follows that the more complicated the interconnection scheme, the less often an individual will actually use the cover. For example, after activity where goggles are worn, such as snow skiing, users will usually move their goggles above their eyes and rest them on their forehead or helmet. Alternatively, user's will position their goggles around their neck, throw them in a bag, or store them in a coat or pants pocket. Goggles can be damaged in any of these post-use situations. Nevertheless, user's will avoid using a complex goggle cover, even when they know that failure to properly cover and protect their goggles will likely lead to damage.

An example of a goggle cover that is difficult to interconnect is found in U.S. Patent Application 2009/0026095, which discloses a protective cover that wraps entirely around the goggle. This cover configuration requires that a wearer remove their goggles from their head or helmet to interconnect the cover to the goggle. Further, U.S. Pat. No. 6,907,617 discloses a goggle lens shield that requires an elastic drawstring to interconnect the cover to the goggle. The elastic drawstring is kept in place by locking devices positioned on either side of the goggle near the strap. To attach the cover one must take the thin elastic chord out of the locking device, wrap it around the strap and then put the thin elastic chord through a small opening in the locking device. This manner of connection takes precision and is difficult to perform when wearing gloves.

It is thus a long felt need to provide a lens cover that is easy to install onto a pair of goggles and which will promote the use of the cover. Further, it is desirable to combine a lens cloth with the cover so that wearer will be encouraged to use the proper lens cleaning material. The following disclosure describes an easy to install goggle cover that possesses an integrated lens cleaning cloth.

SUMMARY OF THE INVENTION

It is one aspect of the present invention to provide a goggle with an integrated cleaning cloth. More specifically, one embodiment of the present invention provides a cover that conceals at least an outer surface of the goggle lens. The portion of the cover that is located adjacent to the outer surface of the lens is made of a material that will not damage the lens, such as microfiber or other lens-safe material. Alternatively, or in addition to incorporating microfiber or similar material into the cover, a lens cloth may be selectively associated with the cover.

The cover of one embodiment of the present invention is generally comprised of a primary panel, an upper panel, and a lower panel when installed, the primary panel contacts the outer lens surface of the goggles, the top panel engages a top portion of the goggles, and the bottom panel engages to the bottom portion of the goggles to substantially envelope the goggles, especially those portions that could be easily damaged. Further, the top and bottom panels of some embodiments of the present invention include a resilient inner edge made of an elastomeric material that helps compress the panels of the cover around the goggles. The cover also includes connecting members for selective interconnection to the strap or other portions of the goggles. The size of the goggle cover, along with the elastomeric seams, allows the cover to stretch to fit most snow sports, tactical, or motor sports goggles.

It is another aspect of embodiments of the present invention to provide a cover that is easy to interconnect and disconnect to the goggles. One embodiment of the present invention includes resiliently deflectable clips that are similar in construction to hair clips. Such resiliently deflectable clips are described in U.S. Pat. Nos. 2,106,561, 3,416,202, 4,793,030, 3,677,270, 3,898,717, and 5,722,437, U.S. Patent Application Publication No. 2004/0182412, and WIPO Publication No. WO2006/003415, which are incorporated by reference herein. In operation the clips open to receive a goggle strap. Once the goggle cover is in place, the clips are deflected inwardly to secure the cover onto the goggles and the associated strap.

One of skill in the art will appreciate that different interconnection mechanisms may be incorporated without departing from the scope of the invention. For example, the cover may include magnets that engage onto metallic segments incorporated into the goggles or strap. Alternatively, the goggles or its associated strap may possess a magnetic material that selectively interconnects with metallic portions of the cover. The magnet or metallic material may be incorporated into a member that is selectively connected onto an existing pair of goggles. Similarly, the cover may be interconnected to the goggles by way of hook and loop fasteners, i.e., Velcro®. More specifically, instead of spring-banded metal connecting devices as employed by some embodiments, webbing may be incorporated into the lateral portions of the cover. In operation, the webbing would be wrapped around the goggle and connect to itself, somewhat like the connection mechanism disclosed in U.S. Pat. No. 6,907,617 to Johnson, which is incorporated by reference herein. Further, the goggle cover may be interconnected to the goggles with connecting members similar to a plastic or metallic belt clips or the goggle cover may possess elastic lateral edges and function similar to a shower cap that fits around the goggle face, which omits the need for a connecting member, or mechanism.

It is another aspect of the present invention to provide a cover that is easily stored. In one embodiment of the present invention, the cover is made of a soft, resilient fabric that is easily folded into a compact shape. Some embodiments of the present invention also employ a pouch that is selectively interconnected to the strap of the goggles, or integrated therein, that can receive a folded cover.

It is another aspect of the present invention to provide cleaning cloth that also may function as a goggle protector. More specifically, some embodiments of the present invention include a cleaning cloth that is associated with the top panel of the goggle cover. The cleaning cloth thus is able to at least partially conceal the inner lens surface when the cover is installed on the goggles. The cleaning cloth may be comprised of two separate materials, a microfiber for cleaning the inner and outer lens surfaces and a water resistant material similar to that of the outer surface of the primary panel, the top panel, and the bottom panel. In this example, an inner surface of microfiber would be positioned adjacent to the inner lens surface when the cover is installed. The cleaning cloth may also include an interconnection mechanism located on a bottom edge thereof that selectively interconnects to at least one of the bottom panel, primary panel, or top panel of the goggle cover using similar mechanisms as described in U.S. Patent Application Publication No. 2009/0026095, which is incorporated by reference herein. By completely wrapping around the goggles, enhanced protection is provided.

It is another aspect of the present invention to provide a cover that has a removable cleaning cloth that is selectively interconnected to the primary panel, top panel, or bottom panel of the cover. The lens cloth may be interconnected to the panel by way of hook and loop fasteners or similar interconnection mechanisms. As such, the cleaning cloth may be replaced when it becomes worn or lost, for example.

It is another aspect of the present invention to provide a cover that is aesthetically pleasing. More specifically, one embodiment of the present invention includes a primary panel comprised of a material that receives artistic designs and indicia. Further, the top and bottom panels may also receive art work or advertisements.

It is thus one aspect of the present invention to provide a cover adapted for selective interconnection to a pair of goggles, comprising: a primary panel adapted for engagement to a lens portion of the goggles; a top panel adapted for selective engagement to a top portion of the goggles having a first edge interconnected to a top edge of said primary panel and a second edge; a cleaning cloth interconnected to said second edge of said top panel; a bottom panel adapted for selective engagement to a bottom portion of the goggles having a first edge interconnected to a bottom edge of said primary panel; a first connector associated with a left edge of said primary panel; a second connector associated with a right edge of said primary panel; and wherein said first connector and said second connector are adapted to selectively interconnect to a strap that is associated with the goggles such that the primary panel engages the goggle lens, the top panel engages the top portion of the goggles, and the bottom panel engages the bottom portion of the goggles.

It is still yet another aspect of the present invention to provide a cover adapted for selective interconnection to a pair of goggles, comprising: a primary panel adapted for selective engagement to a lens portion of the goggles; a cleaning cloth associated with said primary panel; a first means for connecting associated with a left edge of said primary panel; and a second means for connecting associated with right edge of said primary panel.

It is another aspect of the present invention to provide a combination comprising: a pair of goggles having a lens bounded by a frame comprised of a top portion, a bottom portion, a left portion, and a right portion, said lens being spaced from an inner surface of the frame that is adapted to contact a user's face, said goggles also comprising a strap that is associated on one end to a left side of said frame and on another end to a right side of said frame; a cover adapted for selective interconnection to said pair of goggles, comprising: a primary panel adapted for selective engagement to said lens, said primary panel associated with a cleaning cloth; a first means for connecting associated with a left edge of said primary panel; a second means for connecting associated with right edge of said primary panel.

Further, it is an aspect of the present invention to provide a method of protecting a lens of a pair of goggles, comprising: positioning the front panel of a protective cover over an outer surface of said lens; positioning a first portion of said protective cover on the top of said goggles; positioning the second portion of said protective cover on the bottom of said goggles; positioning a first lateral edge of said protective cover adjacent to a lateral edge of the goggles; attaching a connecting mechanism associated with said first lateral edge of said protective cover onto the strap of the goggles; positioning one of a second lateral edge of said protected cover adjacent to a lateral edge of the goggles; and attaching a connecting mechanism associated with said second lateral edge of said protective cover onto the strap of the goggles.

The Summary of the Invention is neither intended nor should it be construed as being representative of the full extent and scope of the present invention. Moreover, references made herein to "the present invention" or aspects thereof should be understood to mean certain embodiments of the present invention and should not necessarily be construed as limiting all embodiments to a particular description. The present invention is set forth in various levels of detail in the Summary of the Invention as well as in the attached drawings and the Detailed Description of the Invention and no limitation as to the scope of the present invention is intended by either the inclusion or non-inclusion of elements, components, etc. in this Summary of the Invention. Additional aspects of the present invention will become more readily apparent from the Detail Description, particularly when taken together with the drawings.

BRIEF DESCRIPTION OF THE DRAWINGS

The accompanying drawings, which are incorporated in and constitute a part of the specification, illustrate embodiments of the invention and together with the general description of the invention given above and the detailed description of the drawings given below, serve to explain the principles of these inventions.

To assist in the understanding of one embodiment of the present invention the following list of components and associated numbering found in the drawings is provided herein:

2 Goggle cover
6 Primary panel
10 Top panel
14 Bottom panel
18 Connecting member
22 Lens
26 Goggles
30 Rear surface
34 Elastomeric member 38 Lens frame
42 Rear edge of the top panel
46 Rear edge of the bottom panel
47 Top portion
48 Bottom portion
50L Left pocket
50R Right pocket
52 Lateral edge
58 Strap
62 Lens cleaning cloth It should be understood that the drawings are not necessarily to scale. In certain instances, details that are not necessary for an understanding of the invention or that render other details difficult to perceive may have been omitted. It should be understood, of course, that the invention is not necessarily limited to the particular embodiments illustrated herein.

DETAILED DESCRIPTION

Referring now to FIGS. 1-5, a goggle cover 2 comprising a primary panel 6, a top panel 10, a bottom panel 14 and associated connecting mechanisms is shown 18. In operation, the primary panel 6 is placed adjacent to a lens 22 of a pair of goggles 26 such that a rear surface 30 of the primary panel 6 is engaged onto the lens portion 22 of the goggles 26.

Figure 1:
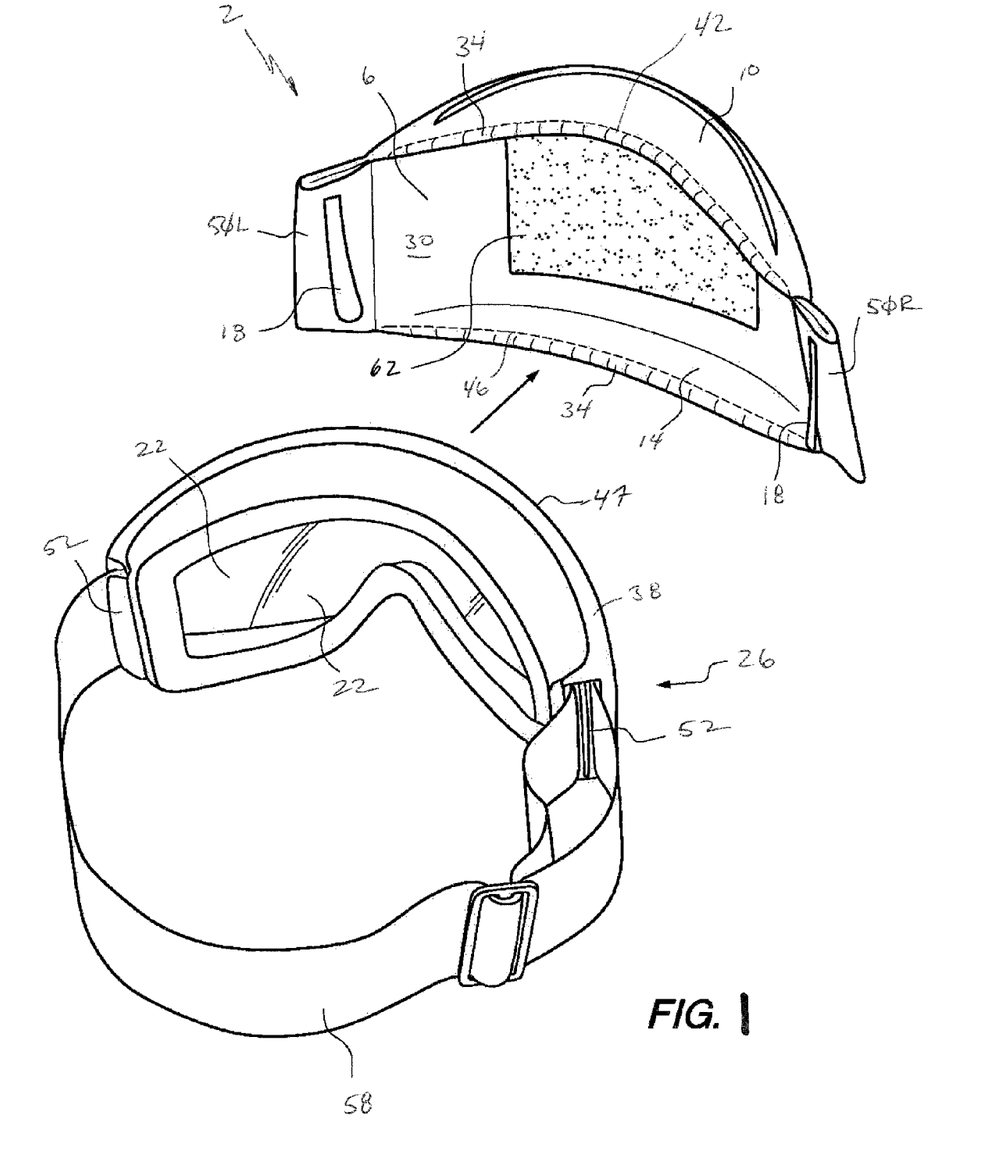
FIG. 1 is a rear perspective view showing the cover of one embodiment positioned away from a pair of goggles.
Figure 2:
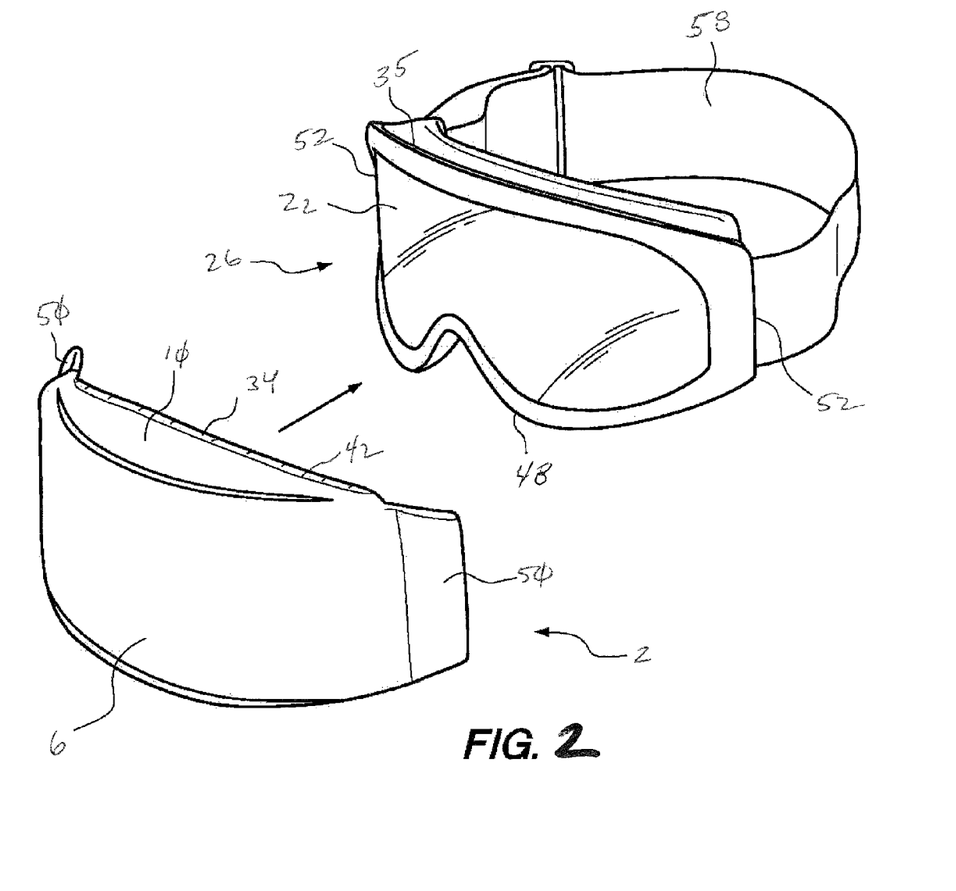
FIG. 2 is a front perspective view similar to FIG. 1.

Referring now specifically to FIG. 1, the cover 2 is shown spaced from the goggles 26. Again, the cover 2 comprises the top panel 10 and the bottom panel 14 that are separated by the primary panel 6. One skilled in the art will appreciate that the top panel 10 and bottom panel 14 are not necessarily required but are employed to enhance engagement of the primary panel 6 to the lens 22. The primary panel 6 is contoured to generally correspond to the contour of the goggles 26 and associated lens. The width of the cover 2 is, preferably, not much larger than the width of the lens frame 38. For example, the cover 2 of some embodiments is about two and a half inches wider than the lens frame 38 when the goggle cover 2 is stretched.

More specifically, goggle sizes within industries such as snow sports, motor sports, and tactical vary in sizes slightly, therefore, the goggle cover material preferably will be made of neoprene laminated with a tightly woven material with enough flexibility to contour to the shape of various goggles. Such material provides durability plus a tight weave that will prevent large particles of dirt and debris from penetrating the cover. However, it is to be understood that other suitable types of fabric or material may be used. For example, although the cover 2 is described herein as being made of a soft, flexible material, one skilled in the art will appreciate that a more rigid goggle cover may be employed without departing from the scope of the invention.

The top panel 10 and the bottom panel 14 include an elastomeric member 34 that helps maintain engagement of the primary panel 6 onto the goggles 26. The elastomeric members 34 contour to the shape of the goggle 26 and are sewn or otherwise integrated into the rear edge 42 of the top panel 10 and the rear edge 46 of the bottom panel 14. Because the goggle cover 2 is fabric, it may be folded over the elastomeric member 34 to create a seam. Elastomeric members 34 are preferably between about ¼ inch and ½ inch thick and allow the goggle cover 2 to stretch to fit most sizes of goggles. The elastomeric members also help to cup the top portion 47 and the bottom portion 48 to help insure a secure attachment of goggle cover 2.

To further interconnect the goggle cover 2 to the goggles 26, one embodiment of the present invention includes a left pocket 50L and a right pocket 50R. Each pocket 50 is associated with a corresponding connecting member 18 that selectively engages a goggle strap 58. The connecting member 18 does not necessarily have to interconnect with the strap 58. More specifically, one of skill in the art will appreciate the connecting members 18 may interconnect to other portions of the goggles 26, such as the lens frame 38 or may interconnect with corresponding connecting members or mechanisms associated with the goggles 26. Furthermore, the connecting members 18 may be associated with the top panel 10, primary panel 6, or bottom panel 14 of the cover.

Figure 4:
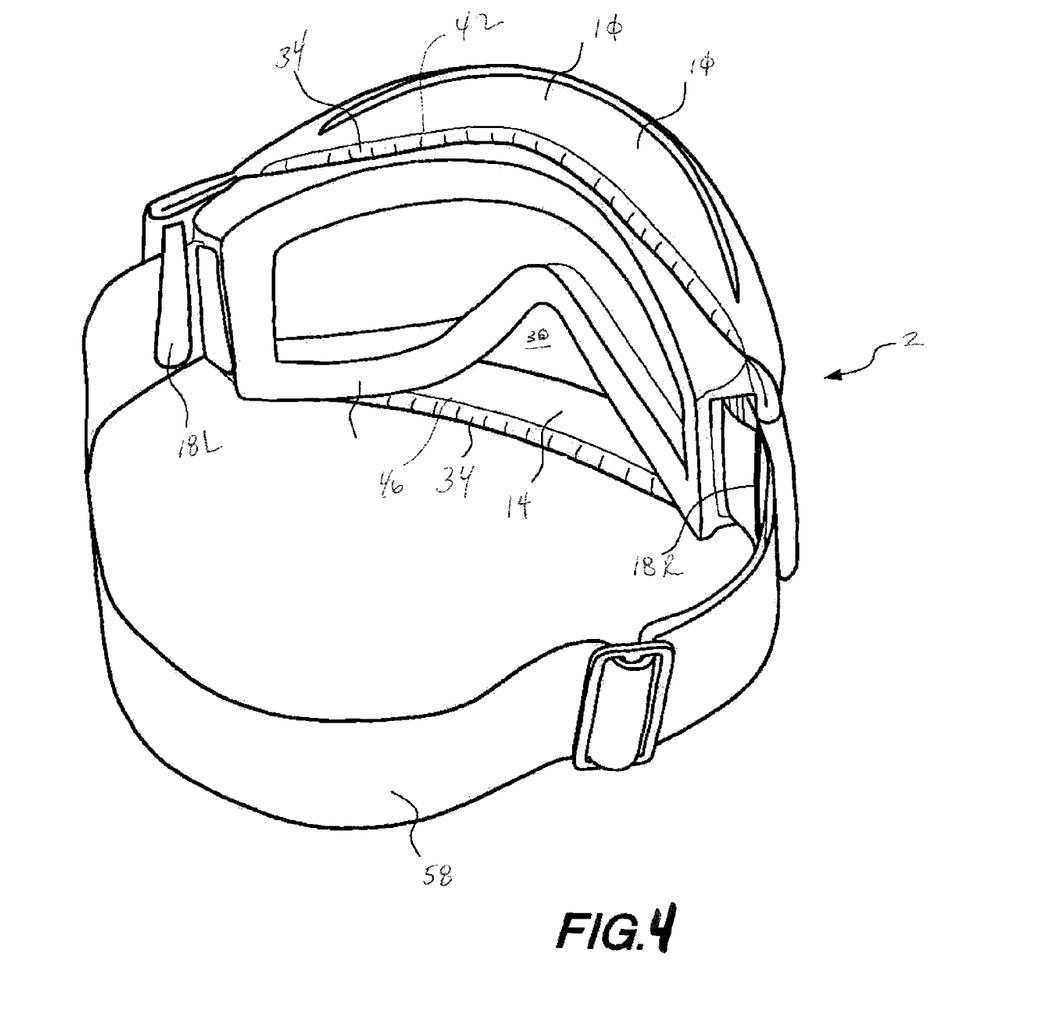
FIG. 4 is a front perspective view showing the cover installed onto the goggles.

The utility of the connecting mechanism 18 is further illustrated in FIG. 4 where connecting members 18 are shown fastened onto the strap 58 just beyond the lateral edges 52 of the lens frame 38. Preferably, the connecting members 18 will be comprised of a resilient metallic material that can open and close easily. An example of such a mechanism is a snap clip used to maintain hair in a predetermined style. One design benefit of the connecting members 18 is that they retract so projections are reduced, which helps maintain a pocket-sized goggle cover. The contemplated clip will preferably be a custom design for the goggle cover 42, and will be coated with a protective rubber, silicone, epoxy or other types of plastic, which will insure that the connecting member 18 will not scratch the lens 22 of the goggle 26 when opened. When the cover is installed, the top panel 10 will rest on the top portion 47 of the goggles and the goggle panel 14 will rest against the bottom portion 48 of the goggles.

As shown in FIG. 1, the goggle cover 2 may include a lens cloth 62 associated with the rear edge 42 of the top panel 40. Alternatively, the cleaning cloth 62 may be removably interconnected to the rear edge 42 or the rear surface 30 of the primary panel 6, thereby allowing it to be replaced if lost or damaged. In one embodiment of the present invention, the lens cloth 62 is interconnected to the rear edge 42 of the top panel 40 wherein no portion of the lens cloth 62 is interconnected to the rear, inner surface 30 of the primary panel 6. The cleaning cloth 62 is, preferably, made of a microfiber of at least about 600 denier that is effective in removing dirt, dust, oils, etc. from the lens. Microfiber is also absorbent, which is helpful in the snowy environments wherein the goggle cover may be used. This absorbency helps the wearer wipe the goggle lenses of water and snow before applying the goggle cover.

Figure 3:
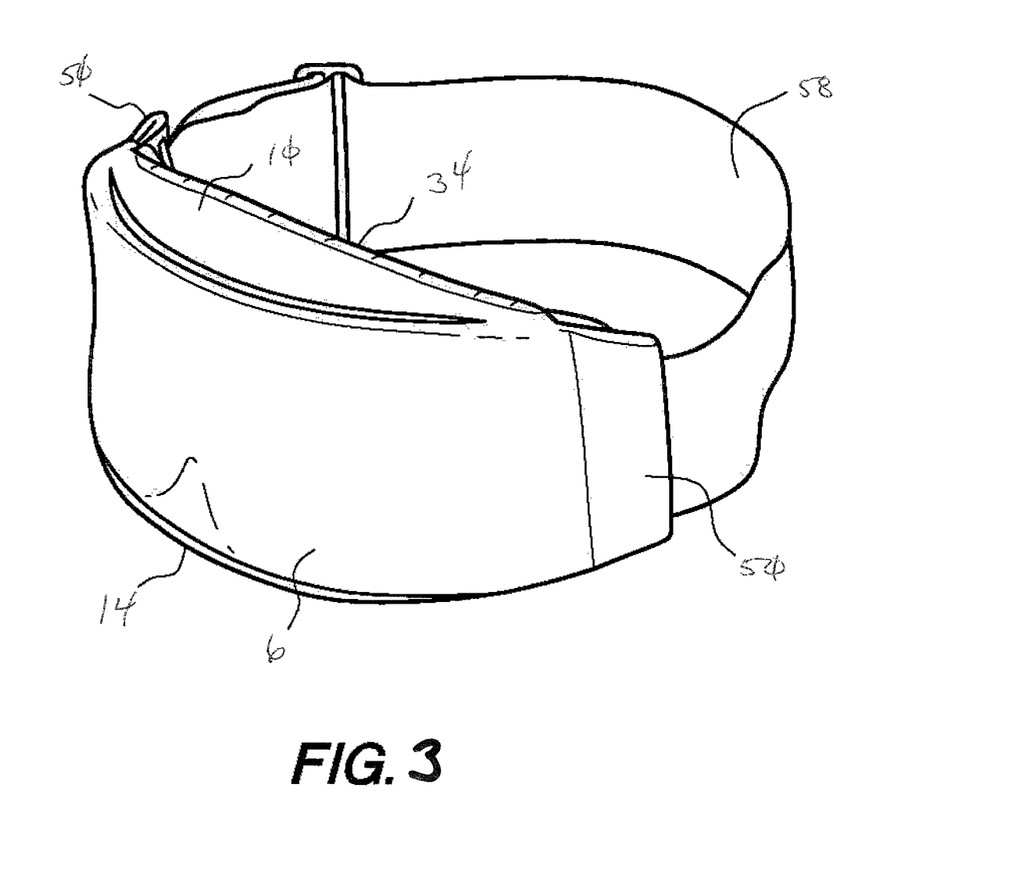
FIG. 3 is a rear perspective view showing the cover installed onto the goggles.

FIGS. 3 and 4 show the lens cover 2 interconnected to the goggles 26. Here, the left and right pockets 50 are associated with corresponding lateral edges 52 of the goggles 26 and the connecting members 18 have been closed wherein the strap 58 is positioned between the connecting member 18 and the pocket 50. Further, FIG. 4 shows the bottom panel 14 of the cover 2 associated with a bottom portion 48 of the lens frame and the top panel 10 of the cover 2 is associated with a top portion of the lens frame. The primary panel 6 is thus securely engaged onto the lens 22 wherein the elastomeric members 14 associated with the top panel 10 and the bottom panel 14 maintain the shape and interconnection of the primary panel 6 with respect to the lens.

To connect the cover 2 to the goggles 26, the wearer must open the left connecting member 18L by pushing a mid-section thereof (see FIG. 1, for example). When opened, a space is provided between the pocket 50 and the connecting mechanism 18 that receives the strap 58. Once the strap 58 is positioned within the space, the left connecting member 18L is moved to a closed position (see FIG. 4). When closed, the cover 2 is secured to the left lateral edge of the goggles such that the cover 2 may be stretched to position the right connector mechanism 18R adjacent to the right lateral edge of the lens frame, which will also position the primary panel against the lens. Stretching the cover over the goggles will also position the top panel 10 and the bottom panel 14 against the top portion 47 and the bottom portion 48 of the goggle, respectively. The right connecting member 18R is then interconnected to a corresponding portion of the strap 58.

To detach goggle cover 2, the wearer opens on the left connecting mechanism 18L and slides goggle strap 58 away. Next, the right connecting member 18R is opened and the goggle strap 58 removed. The connecting mechanisms 18 are then closed in preparation for stowage of the cover 2 in pocket or elsewhere.

Figure 5:
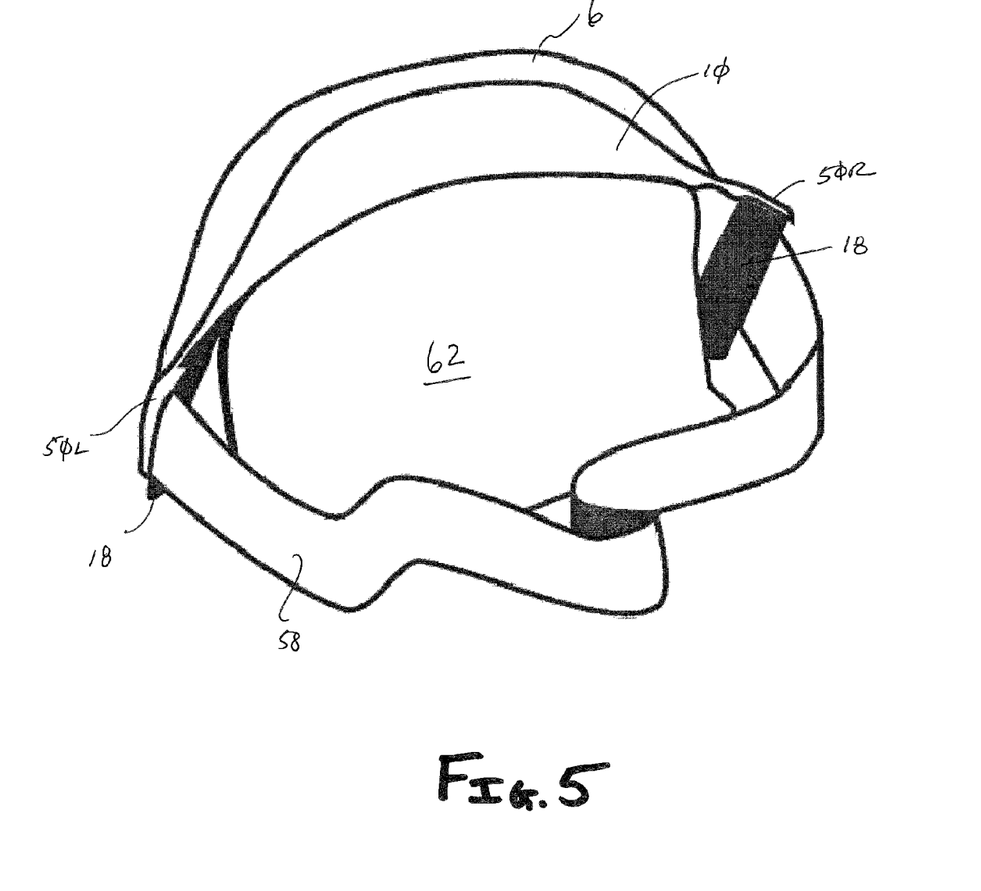
FIG. 5 is a rear perspective view showing the cover installed onto the goggles wherein a cleaning cloth is positioned so as to conceal an inner surface of the lens.

FIG. 5 shows the goggle cover 2 installed on goggles wherein the cleaning cloth 62 is positioned in such a way to conceal the inner surface of the lens. In this embodiment the cleaning cloth 62 functions as an auxiliary goggle protector that prevents the goggle strap 58 from contacting the inner surface of the lens. The cleaning cloth 62 may be comprised of two separate materials, an inner surface fabricated of a material for cleaning the lens surfaces and an outer surface fabricated of a water resistant material.

While various embodiments of the present invention have been described in detail, it is apparent that modifications and alterations of those embodiments will occur to those skilled in the art. However, it is to be expressly understood that such modifications and alterations are within the scope and spirit of the present invention, as set forth in the following claims. Further, the invention(s) described herein is capable of other embodiments and of being practiced or of being carried out in various ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

What is claimed is:

1. A cover adapted for selective interconnection to a pair of goggles, comprising:
    a primary panel adapted for engagement to a lens portion of the goggles, said primary panel having an inner surface that is adapted to contact an outside surface of the lens portion;
    a top panel adapted for selective engagement to a top portion of the goggles, said top panel having a first edge interconnected to a top edge of said primary panel and a second edge;
    a cleaning cloth interconnected to said second edge of said top panel and spaced from said inner surface such that no portion of said cleaning cloth is interconnected to said inner surface of said primary panel;
    a bottom panel adapted for selective engagement to a bottom portion of the goggles, said bottom panel having a first edge interconnected to a bottom edge of said primary panel and a second edge;
    a first connector associated with a left edge of said primary panel;
    a second connector associated with a right edge of said primary panel; and
    wherein said first connector and said second connector are adapted to selectively interconnect to a strap that is associated with the goggles such that the primary panel engages the goggle lens, the top panel engages the top portion of the goggles, and the bottom panel engages the bottom portion of the goggles.

2. The cover of claim 1, wherein said second edge of said top panel and said second edge of said bottom panel are comprised of an elastomeric material.

3. The cover of claim 1, wherein said cleaning cloth is selectively interconnected to said top panel.

4. The cover of claim 1, wherein when installed said cleaning cloth is adapted to conceal at least a portion of an inner surface of the lens portion of the goggles, thereby increasing protection provided by said cover.

5. The cover of claim 1 wherein said first connector and said second connector are comprised of resiliently deflectable clips.

6. The cover of claim 5, wherein said clips are at least partially surrounded with a protective cover.

7. A cover of claim 6, wherein said protective cover is comprised of at least one of webbing, rubber, foam, plastic, silicone, epoxy, and PVC.

8. The cover of claim 1 wherein said cleaning cloth includes a bottom edge for selective interconnection to at least one of said bottom panel and said top panel.

9. The cover of claim 1, wherein said primary panel, top panel, and bottom panel are fabricated from one piece of fabric.

10. A cover adapted for selective interconnection to a pair of goggles, comprising:
    a primary panel adapted for selective engagement to a lens portion of the goggles, said primary panel having an inner surface that is adapted to contact an outside surface of the lens portion;
    a top panel having a first edge interconnected to a top edge of said primary panel and a second edge;
    a bottom panel having a first edge interconnected to a bottom edge of said primary panel and a second edge;
    a cleaning cloth interconnected to said second edge of said top panel and spaced from said inner surface such that no portion of said cleaning cloth is interconnected to said inner surface of said primary panel;
    a first means for connecting associated with a left edge of said primary panel; and
    a second means for connecting associated with right edge of said primary panel.

11. The cover of claim 10, wherein said cleaning cloth is selectively interconnected to said second edge of said top panel.

12. The cover of claim 10, wherein said second edge of said top panel and said second edge of said bottom panel are comprised of an elastomeric material.

13. The cover of claim 10, wherein said first means for connecting and said second means for connecting are comprised of resiliently deflectable clips.

14. A combination comprising:
    a pair of goggles having a lens bounded by a frame comprised of a top portion, a bottom portion, a left portion, and a right portion, said lens being spaced from an inner surface of the frame that is adapted to contact a user's face, said goggles also comprising a strap that is associated on one end to a left side of said frame and on another end to a right side of said frame;
    a cover adapted for selective interconnection to said pair of goggles, comprising:
        a primary panel adapted for selective engagement to said lens, said primary panel associated with a cleaning cloth, said primary panel also having an inner surface that is adapted to contact an outside surface of the goggle lens;
        a top panel having a first edge interconnected to a top edge of said primary panel and a second edge;
        a bottom panel having a first edge interconnected to a bottom edge of said primary panel and a second edge;

a first means for connecting associated with a left edge of said primary panel;

a second means for connecting associated with right edge of said primary panel; and wherein said cleaning cloth is interconnected to said second edge of said top panel and spaced from said inner surface such that no portion of said cleaning cloth is interconnected to said inner surface of said primary panel.

15. The combination of claim 14, wherein said second edge of said top panel and said second edge of said bottom panel are comprised of an elastomeric material.

16. The combination of claim 14, wherein said first means for connecting and said second means for connecting are comprised of clips.

* * * * *